(12) United States Patent
DaQuino et al.

(10) Patent No.: US 8,213,069 B2
(45) Date of Patent: Jul. 3, 2012

(54) COMPENSATING FOR VOICE COIL THERMAL EXPANSION IN A MICROARRAY SCANNER

(75) Inventors: Lawrence J. DaQuino, Los Gatos, CA (US); Edwin de Groot, Saratoga, CA (US); Donald J. Schremp, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 392 days.

(21) Appl. No.: 12/494,041

(22) Filed: Jun. 29, 2009

(65) Prior Publication Data

US 2010/0328746 A1  Dec. 30, 2010

(51) Int. Cl.
*G02B 26/08* (2006.01)
(52) U.S. Cl. .................................. 359/210.1; 359/221.2
(58) Field of Classification Search ............... 359/209.1, 359/210.1, 221.2, 811, 813, 814, 819, 820, 359/822–824, 900
See application file for complete search history.

(56) References Cited

U.S. PATENT DOCUMENTS

| | | | |
|---|---|---|---|
| 4,257,450 A | 3/1981 | Ollivier | |
| 4,349,177 A | 9/1982 | Shimada et al. | |
| 4,696,612 A | 9/1987 | Germond et al. | |
| 5,331,469 A * | 7/1994 | Andrews | 359/824 |
| 5,650,986 A * | 7/1997 | Lee et al. | 369/44.14 |
| 5,900,995 A * | 5/1999 | Akada et al. | 359/824 |
| 7,279,814 B2 | 10/2007 | Patt et al. | |
| 7,336,409 B2 | 2/2008 | Sissom | |
| 7,448,518 B2 | 11/2008 | Yue | |
| 7,501,615 B2 | 3/2009 | Cleveland et al. | |
| 7,538,959 B1 | 5/2009 | Wheeler | |
| 8,004,774 B2 * | 8/2011 | Yasuda | 359/700 |
| 8,077,411 B2 * | 12/2011 | Shyu et al. | 359/823 |
| 2008/0198485 A1 * | 8/2008 | Kosmowski | 359/811 |
| 2011/0026150 A1 * | 2/2011 | Shyu et al. | 359/824 |

* cited by examiner

*Primary Examiner* — Frank Font (57) ABSTRACT

A lens stage for use in a scanning system is provided. In certain embodiments, the lens stage comprises: a) a support comprising a first rail and a second rail, in which the first rail and the second rail are mounted to the support in parallel; and b) a linearly moveable lens assembly comprising: i) a voice coil comprising a moving coil that moves in a direction parallel to the rails; ii) a lens; iii) a bracket that is attached to: a) the moving coil and b) the lens, and moveably engaged with the rails via a set of bearing cars; and iv) means to reduce force exerted on the set of bearing cars due to thermal expansion of the moving coil.

17 Claims, 3 Drawing Sheets

COMPENSATING FOR VOICE COIL THERMAL EXPANSION IN A MICROARRAY SCANNER

INTRODUCTION

Arrays of surface-bound binding agents may be used to detect the presence of particular targets, e.g., biopolymers, in solution. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

Binding interaction or complexes of binding pairs are detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As such, optical scanners play an important role in many array based applications. Optical scanners act like a large field fluorescence microscope in which the fluorescent pattern caused by binding of labeled molecules on the array surface is scanned. In this way, a laser induced fluorescence scanner provides for analyzing large numbers of different target molecules of interest, e.g., genes/mutations/alleles, in a biological sample.

An integral component of an array scanner contains a linear forcer, a bearing system, brackets which generally hold a lens and a mirror, and position feedback system.

As array density increases, the need for higher resolution scans becomes critical. With the smaller pixel size and increased number of scan lines comes an increase in scan time. One of the most effective ways of reducing the scan time is to increase the acceleration of the linear forcer since there is no scanning performed during the turnaround time.

This disclosure relates in part to a device for a scanner system.

SUMMARY OF THE INVENTION

A lens stage for use in a scanning system is provided. In certain embodiments, the lens stage comprises: a) a support comprising a first rail and a second rail, in which the first rail and the second rail are mounted to the support in parallel; and b) a linearly moveable lens assembly comprising: i) a voice coil comprising a moving coil that moves in a direction parallel to the rails; ii) a lens; iii) a bracket that is attached to: a) the moving coil and b) the lens, and moveably engaged with the rails via a set of bearing cars; and iv) means to reduce force exerted on the set of bearing cars due to thermal expansion of the moving coil.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

An "array," or "chemical array" includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. No. 5,599,695, U.S. Pat. No. 5,753,788, and U.S. Pat. No. 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). If a device is "in communication with" another device, the devices are capable of transmitting or data or instructions to each other. Such devices may be networked to each other. "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top", "upper", and "lower" are used in a relative sense only.

A "scanner" is device for evaluating arrays. In scanners, an optical light source, particularly a laser light source, generates a collimated beam. The collimated beam is focused on the array and sequentially illuminates small surface regions of known location (i.e. a position) on an array substrate. The resulting signals from the surface regions are collected either confocally (employing the same lens used to focus the light onto the array) or off-axis (using a separate lens positioned to one side of the lens used to focus the light onto the array). The collected signals are then transmitted through appropriate spectral filters, to an optical detector. A recording device, such as a computer memory, records the detected signals and builds up a raster scan file of intensities as a function of position, or time as it relates to the position. Such intensities, as a function of position, are typically referred to in the art as "pixels". To achieve the precision required for such activity, components such as the lasers must be set and maintained with particular alignment. Scanners may be bi-directional, or unidirectional, as is known in the art.

The scanner typically used for the evaluation of arrays includes a scanning fluorometer. A number of different types of such devices are commercially available from different sources, such as such as Perkin-Elmer, Agilent, or Axon Instruments, etc., and examples of typical scanners are described in U.S. Pat. Nos. 5,091,652; 5,760,951, 6,320,196 and 6,355,934.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent. The term "evaluating a pixel" and grammatical equivalents thereof, are used to refer to measuring the strength, e.g., magnitude, of pixel signal to determine the brightness of a corresponding area present on the surface of an object scanned.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station. In certain embodiments, a processor may be a "signal processor", where a signal processor receives input signals and processes those signals. A signal processor may be programmed or hard wired to perform one or more mathematical functions, such as those described below. In certain embodiments, a signal processor may "integrate" a set of digital signals (e.g., a set of digital signals representing an analog signal or a digitized version of an analog signal). By "integrating" is meant that a set of digital signals is input into a signal processor and the signal processor provides an output signal, in certain embodiments a single output signal that represents the set of input signals. In many embodiments, the input set of digital signals may be integrated by summing the set of input signals, however, other means for integrating (e.g., averaging, etc.) are well known in the art. If an analog signal is referred to as being integrated, then it is understood that the analog signal is first digitized (i.e., sampled) prior to integration. For example, if an analog signal for a pixel is to be integrated, the signal is first sampled and digitized to provide a set of digital signals, and those digital signals are integrated by a signal processor to provide an output signal, typically a binary signal, that represents a numerical evaluation of the overall magnitude of the input set of digital signals (thereby providing a numerical evaluation of the magnitude of the analog signal for the pixel). The output of a signal processor may be referred herein as "data", and may be stored in memory.

Data from reading an array may be raw data (such as fluorescence intensity readings for each feature in one or more color channels, or, for example, the output of a signal processor that has integrated a set of digital signals for a pixel) or may be processed data such as obtained by rejecting a reading for a feature which is below a predetermined threshold and/or forming conclusions based on the pattern read from the array (such as whether or not a particular target sequence may have been present in the sample). The data obtained from an array reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc. Data may represent a floating point number or integer, for example.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "providing" encompasses such terms as "generating", "identifying" and "producing".

DETAILED DESCRIPTION OF THE INVENTION

A lens stage for use in scanning of a chemical array is provided. In certain embodiments, the lens stage comprises: a) a support comprising a first rail and a second rail, in which the first rail and the second rail are mounted to the support in parallel; and b) a linearly moveable lens assembly comprising: i) a voice coil comprising a moving coil that moves in a direction parallel to the rails; ii) a lens; iii) a bracket that is attached to: a) the moving coil and b) the lens, and moveably engaged with the rails via a set of bearing cars; and iv) means to reduce force exerted on the set of bearing cars due to thermal expansion of the moving coil.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, system and methods aspects of the invention are first described. This discussion is followed by a description of suitable hardware for use in the invention.

Lens Stage

A lens stage is provided. In certain embodiments, the lens stage comprises: a) a support comprising a first rail and a second rail, in which the first rail and the second rail are mounted to the support in parallel; and b) a linearly moveable lens assembly comprising: i) a voice coil comprising a moving coil that moves in a direction parallel to the rails; ii) a lens; iii) a bracket that is attached to: a) the moving coil and b) the lens, and moveably engaged with the rails via a set of bearing cars; and iv) means to reduce force exerted on the set of bearing cars due to thermal expansion of the moving coil.

Figure 1A:
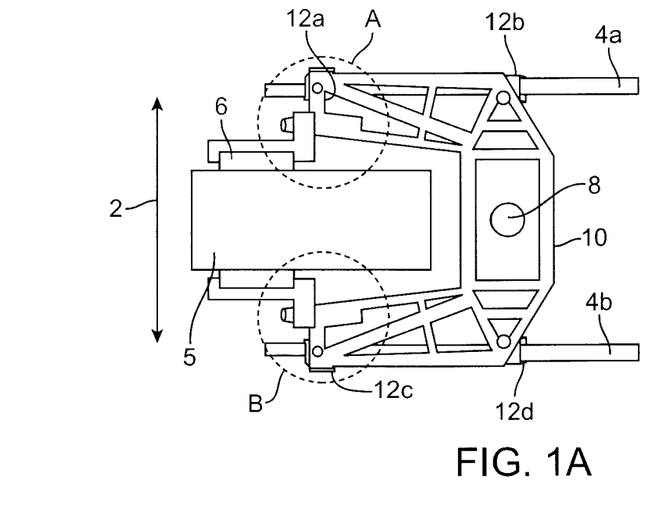
FIGS. 1A-1C depict certain features of the lens stage according to the present disclosure.
Figure 1B:
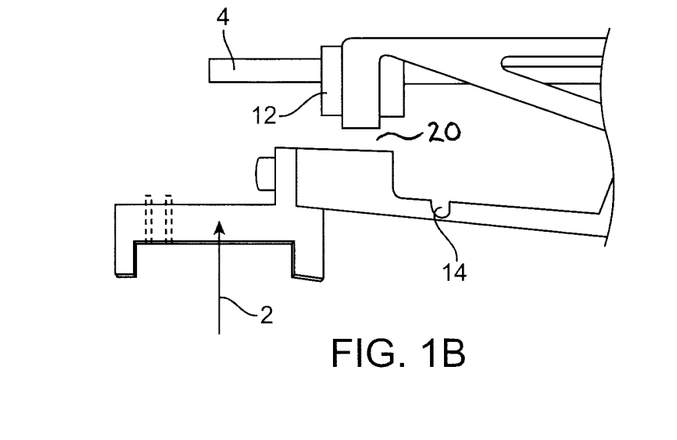
Figure 1C:
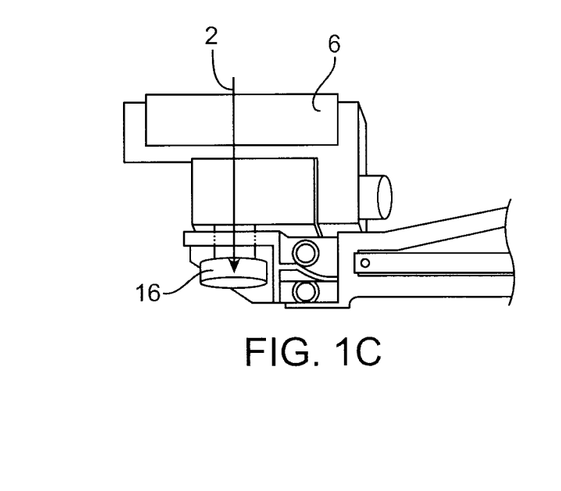

Certain features of the subject lens stage are illustrated in FIG. 1. FIG. 1A shows an exemplary dual rail lens stage system in which the bearing cars that are adjacent to moving coil 6 are connected to the moving coil via conventional means A and B (i.e. without a means to reduce force exerted on the bearing cars due to thermal expansion of the moving coil). FIGS. 1B and 1C illustrate detailed views of means that may be incorporated into the lens stage of FIG. 1A at positions pointed out by dashed circles. The connection shown in FIG. 1B, which illustrates a bracket containing flexure 14, may be incorporated at position A in FIG. 1A, and the connection shown in FIG. 1C, which illustrates a shoulder screw 16, may be incorporated at position B in FIG. 1A. The subject lens stage may contain either connection depicted in FIG. 1B or 1C but not both in the same lens stage. In alternative embodiments, the flexure-containing connection shown in FIG. 1B may be used at position B in the device shown in FIG. 1A, and the shoulder screw-containing connection shown in FIG. 1C may be used at position A in the device shown in FIG. 1A As shown in FIG. 1A, the lens stage comprises a lens assembly on a dual rail support system. With reference to FIG. 1A, the lens assembly contains a voice coil comprising an electromagnetic moving coil 6 that moves back and forth in a linear path parallel to the rails (e.g. parallel to the x-direction relative to the Cartesian coordinate shown in FIG. 1A). Bracket 10 is connected to both sides of moving coil 6. The lens assembly is mounted on the two rails 4a and 4b via a set of bearing cars and moves with the moving coil. In the embodiment shown, there are four bearing cars, 12a, 12b, 12c, and 12d, that connect the bracket to the rails. Lens 8 is held in position by bracket 10 so the lens also moves back and forth in a linear path during operation of the lens stage. In general terms, the voice coils contains: a) a moving coil comprising coil of conductive wire that is attached at both ends to a source of electricity; and b) a stationary magnet, where application of a voltage to the coil causes an electromagnetic field that induces movement of the moving coil relative to the magnet, and reversal of the direction of the current flowing through coil changes the polarity of the electromagnetic field and reverses the direction of movement of the moving coil. Voice coils are known in the art and details of which are disclosed in U.S. Pat. Nos. 7,279,814 and 6,815,846, incorporated herein by reference.

The support system on which the linearly moveable lens system described above is mounted comprises first rail 4a and second rail 4b positioned in parallel to each other and also in parallel to the direction of the back and forth movement of the moving coil. Each bearing car in the set (12a, 12b, 12c, and 12d) moveably connects the bracket to one of the two rails. In the embodiment shown, there are two bearing cars (e.g. 12a and 12b) on each rail that secure one side of the bracket onto the rail, one (12a) proximal to the voice coil and another (12b) distal to the voice coil. On the other side of the bracket, there is also a pair of bearing cars (e.g. 12c and 12d), one (12c) proximal to the voice coil and another (12d) distal to the voice coil. In the embodiment shown in FIG. 1A, parts of the bracket connected to the bearing cars proximal to the voice coil (e.g. moving cars 12a and 12c) are also connected to the part of the bracket attached to moving coil 6. In other words, the parts of the bracket proximal to the voice coil are in a closed frame configuration. Various number of bearing cars (e.g. more or less than four bearing cars) are also envisioned. In certain cases, less than four bearing cars may be used depending on how the support rails are organized. For example, three bearing cars may be used in combination with a three rail support system. In certain embodiments, the connectivity of the bracket to the rails may be configured to be symmetrical, where the line of symmetry bisects the voice coil actuator system and runs along the longitudinal axis parallel to the back and forth movement of the voice coil. Other configurations are also envisioned.

In particular embodiments, the lens is positioned in the bracket to be the center of gravity of the linearly moveable lens assembly. The combination of the dual rail support and the lens positioned as the center of gravity may reduce asymmetrical forcing (i.e. force not parallel to the rails) during the movement of the voice coil, and thus minimizing torque on the lens and increasing stability of the lens stage.

During use, the moving coil in the voice coil of the lens stage may expand due to thermal expansion laterally in the direction 2 shown in FIG. 1. When current is applied to operate the lens stage in a scanner system, one or more parts of the voice coil may heat up depending on the length of operation time and the amount of current being applied. As temperature increases, the material from which the moving coil is made may expand in size. Since the bracket is connected with the moving coil and constrained by the bearing cars on the dual rail support system, expansion of the moving coil may push the bearing cars (e.g. bearing cars 12a and 12c in FIGS. 1A and 2) onto the rails. Due to the force exerted on the bearing cars by thermal expansion, efficiency of the movement of the lens system may decrease. The bearing cars may also decrease in their effectiveness in holding the bracket in place on the dual rail support system, leading to instability in the integrity of the lens stage.

In order to compensate for thermal expansion of the moving coil, the lens stage further contains a means to reduce the force exerted on the bearing cars by a thermally expanded moving coil. Several means are contemplated in this disclosure and are described in detail below.

One means to reduce the force on the bearing cars due to thermal expansion contains a flexure in the bracket. This embodiment is illustrated in FIG. 1B. When the moving coil expands, the flexure allows a part of the bracket to bend while minimizing the effect of thermal expansion on the remaining parts of the bracket. If the parts of the bracket connected to the bearing cars have little or no effect caused by the expansion, the effect of thermal expansion on the bearing cars is consequently minimized.

An exemplary bracket having a flexure is shown in FIG. 1B, as a blown-up image of the top dashed circle in FIG. 1A. FIG. 1B illustrates certain features of an embodiment having a flexure as a means to reduce force exerted by a thermally expanded moving coil on the bearing cars. As shown in FIG. 1B, flexure 14 is located in the bracket proximal to the voice coil. As the moving coil expands in direction 2, the expansion may bend the bracket at the flexure to move the part of the bracket proximal to the voice coil (i.e. between the moving coil and the flexure) in the same direction as the expansion. However, the part of the bracket distal to the voice coil beyond the flexure may not be affected by the thermal expansion. In some cases, the bracket containing a flexure as shown in FIG. 1B is configured differently from the bracket seen in FIG. 1A. As shown in FIG. 1A, parts of the bracket proximal to the voice coil may have a configuration of a closed frame. A bracket containing a flexure, however, may have a shape of an open frame, as depicted in FIG. 1B. An open frame encompasses a configuration in which a part of the bracket connected to the bearing car is disconnected from the part of the bracket connected to the moving coil. In other words, the two parts of the bracket are connected distal to the voice coil relative to the location of the flexure but are disconnected proximal to the voice coil. The disconnection is illustrated by gap 20, shown in FIG. 1B. This open frame configuration proximal to the voice coil reduces the movement experienced by the part of the bracket connected to the bearing cars when the thermally expanding moving coil bends at the flexure the part of the bracket connected to the moving coil.

The flexure in the bracket of the subject lens stage may bend in the same plane as the bracket (i.e., in the x-y plane relative to the Cartesian coordinates shown in FIG. 1). In certain cases, the flexure allows little or no bending in the z direction, which is perpendicular to the x-y plane. During thermal expansion of the moving coil, the bracket may be flexed at the flexure so the part of the bracket proximal to the moving coil moves away from the voice coil. Once the moving coil returns to a size prior to thermal expansion, the flexure is capable of allowing the bracket to become unflexed to return to its original shape. In certain embodiments, once the part of the bracket containing the flexure is unflexed, the flexure does not allow the part of the bracket proximal to the moving coil to bend toward the voice coil.

The flexure may be of a variety of dimensions. In certain embodiments, a segment of the bracket containing the flexure may be of a thicker in the z dimension than in other areas of the bracket. The thicker material present at the flexure may restrict flexing motion in two directions, while allowing flexing in the plane of the bracket (i.e. x-y plane of FIG. 1). The material present at the flexure may also restrict the bending motion as to allow part of the bracket proximal to the voice coil to bend away from the voice coil but not towards the voice coil, except in cases to allow the bracket to return to its original, unflexed position. In certain cases, the size of the notch of the flexure depends on the cross-sectional area of the bracket and the distance of the voice coil to the flexure. In designing the flexure, factors that need to be considered include but not limited to the material of the bracket, the range of the motion and the amount of force involved in the thermal expansion of the moving coil. Any other factors that may be contributing to the stress and torque experienced by the bracket may also be considered. Details of how flexure may be designed may be found in Boresi, A P et al. *Advanced mechanics of materials*, John Wiley and Sons, New York, 1993, and Shigley J, *Mechanical Engineering Design*, p 44, International Edition, McGraw Hill, 1986.

Another means to reduce the force exerted by thermally expanded moving coil on the bearing cars contains a precision shoulder screw that connects one end of the bracket to the moving coil (i.e. one end of the bracket that is proximal to the voice coil actuator system). This embodiment is illustrated in FIG. 1C. This one end of the bracket has an orifice that allows the bracket to be slidingly mounted onto the shoulder of the precision shoulder screw. An end of the shoulder screw is connected to the moving coil while the opposite end may comprise a socket head to keep the bracket mounted on the shoulder of the shoulder screw. Since the bracket is free to slide on the shoulder of the shoulder screw, the shoulder screw may move in the direction of the thermal expansion while minimizing any effect of the expansion on the position of the bracket.

FIG. 1C illustrates certain features of a bracket having a precision shoulder screw as a means to reduce force exerted by a thermal expanded moving coil on bearing cars. FIG. 1C is a blown-up image of the bottom dashed circle in FIG. 1A. As shown in FIG. 1C, when the moving coil expands, shoulder screw 16 moves in the direction 2 of the thermal expansion, and the bracket slides on the shoulder of the shoulder screw.

In certain embodiments, the other end of the bracket not mounted on the precision shoulder screw is connected to the moving coil in a fixed position, such that one end of the bracket is connected to moving coil 6 via shoulder screw 16 while the opposite end is connected to moving coil 6 in a fixed position. In such embodiments, thermal expansion of the moving coil allows the direction of the expansion to be away from the fixed bracket connection and toward the end having the shoulder screw. Upon thermal expansion, the shoulder screw slides in the orifice of the bracket outward, as illustrated by arrow 2 in FIG. 1C.

The precision shoulder screw may be connected to the moving coil in a number of different ways, e.g., by a friction fit, by a screw thread or by welding, etc. For example, the precision shoulder screw may be welded to the moving coil at the end of the screw opposite from the socket head. The precision shoulder screw may also be glued to the moving coil using epoxy or other adhesive, for example. Alternatively, it may contain a threaded portion connected to the shoulder of the screw, which mates with a threaded portion in the moving coil. In alternative embodiments, the precision shoulder screw may also be attached to the moving coil via a friction fit, e.g., in the same manner as a dowel.

In certain cases, the shoulder of the screw has a diameter slightly smaller than the diameter of the bracket orifice. Conversely, the orifice of the bracket may also be designed to have a diameter slightly larger than the diameter of the shoulder of the shoulder screw. In some embodiments, the bracket orifice may be the same or 1, 5, 10, 20 microns or more than the largest size tolerance for the size of the shoulder of the shoulder screw. Although the figures illustrate the shoulder of the screw as cylindrical and the orifice as a circular orifice, as long as there is stability in supporting the connection between the bracket and the moving coil and that there is adequate space in the connection to allow sliding movement on the shoulder screw upon thermal expansion, other shapes of the shoulder screw and the corresponding bracket orifice may be designed. For example, hexagonal, oval, or square shapes may also be used. In certain embodiments, the socket cap at the end of the shoulder screw is larger than the bracket orifice such that the socket cap cannot passes through the bracket orifice. As a result, the socket cap may act to restrain the bracket orifice on the shoulder of the shoulder screw. In other cases, the socket cap is not necessary for restraining the bracket orifice on the shoulder. Accordingly, the socket cap at the end of shoulder screw may not have a diameter larger than the diameter of the shoulder. In some cases, the socket cap may have a diameter that is the same or smaller that the minor thread diameter (e.g. that of a set screw) or may be a dowel pin.

Any of the components of the subject lens stage (e.g. bracket, bearing car, shoulder screw, etc.) may be made with a material that provides a certain amount of stiffness while remaining light weight. Materials from which components of the subject lens stage may be made include aluminum, magnesium or alloys thereof. In certain embodiments, any material of low density, such as those of less than 5 g/cm$^3$, less than 4 g/cm$^3$, less than 3 g/cm$^3$, down to less than 2 g/cm$^3$ or less may be used to make one or more components of the subject lens stage.

The expansion of a moving coil in a direction may be less than about 500 microns (e.g. less than about 300 microns, less than about 100 microns, less than about 50 microns, or less than about 25 microns). Means described above may reduce the distance the bracket moves in response to the thermal expansion of the moving coil by at least 90%, at least 80%, at least 50%, at least 30%, thereby reducing the force exerted on the bearing cars.

Figure 2:
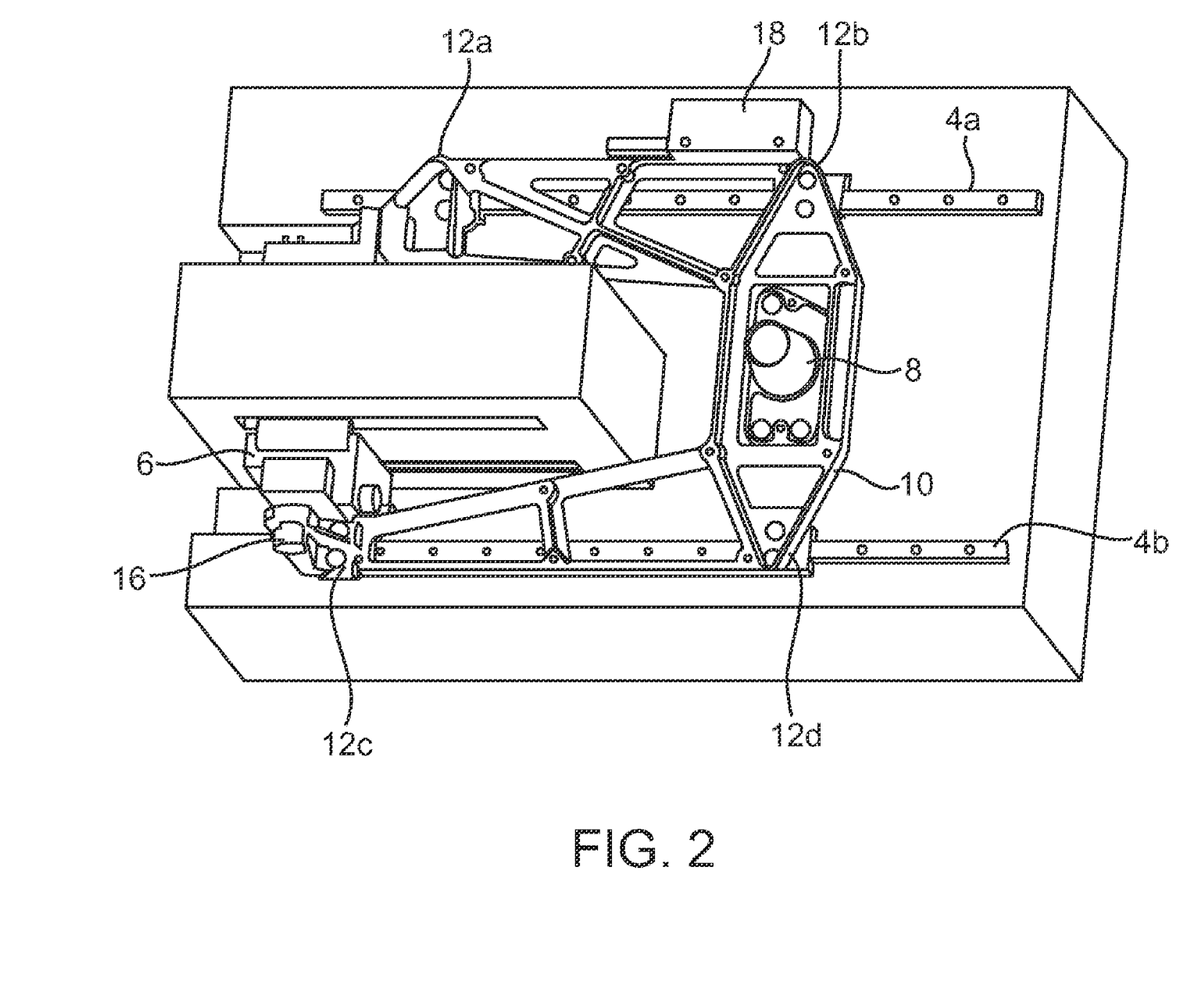
FIG. 2 depicts an oblique view of an exemplary lens stage.

An oblique view of an example of a subject lens stage is shown in FIG. 2, labeled with the same numbering system as described above for FIGS. 1A and 1C. In this example, the shoulder screw is shown as the means to reduce force exerted on the set of bearing cars due to thermal expansion of the moving coil. As noted above, a flexure may be used instead of the shoulder screw, also as a means to reduce force exerted on the bearing cars due to thermal expansion of the moving coil.

As shown in FIGS. 1A and 2, the lens stage moves back and forth in a direction parallel to the rails due to the movement of the moving coil. The moving coil is assembled in a stationary structure in and/or around the moving coil, e.g. a cylindrical moving coil slidingly mounted on a rod. A power source drives a current with alternating polarity through coils of wire wrapped around the moving coil. In the context of a magnetic field generated by permanent magnets fixed in the stationary structure, the current in the coils of wire generate the motive force for the moving coil. Upon application of this current in one polarity, the moving coil moves in one direction. When the current polarity is reversed, the moving coil moves in an opposite direction. Rapid alternating current then leads the moving coil to move in alternating directions in a fast pace. As a result, the lens mounted in the bracket of the lens stage is able to transmit and collect light signals in a plurality of locations in rapid succession. Also shown in FIG. 2 is a linear encoder 18 mounted on a bracket near the lens. The linear encoder is a photo-detecting device that is part of the laser path. It detects the position of the moving bracket and can communicate positional information to other components of the lens stage or a scanner. In some cases, the linear encoder is a self contained unit.

During operation of the lens stage, the positional information would be important to maintain control of the motion speed and range of the lens stage, as will be described in more detail below.

Scanner System

The lens stage described above may be employed in a scanner system. In certain embodiments, the scanner system is a chemical array scanner comprising: a) a light source; b) a stage for holding a chemical array; c) the subject lens stage described previously; and d) a photodetector. The system is configured so that light from the light source passes through the lens of the lens stage to a chemical array positioned in the array-holding stage, and that light emitted by the chemical array passes through the lens of the lens stage and is detected by the photodetector.

In certain embodiments, the light source of the subject system is a laser excitation system that causes light to be emitted from the surface of an array. The system may also contain hardware for performing scanning. A storage medium for storing data produced by scanning may also be included. A scanner may also contain or communicate with a processor including programming for executing scanning and data collection. Since array scanners typically measure at least two, and sometimes three, four, or five, or more wavelengths of light from the surface of an array, the subject scanner may have a corresponding number (e.g., 2, 3, 4, 5, or more) of systems for performing executing the scanning. In many embodiments, the subject scanner contains at least two such systems, corresponding to the "red" and "green" channels of light emitted in typical array experiments, for example (Cheung et al., Nature Genetics 1999, 21: 15-19).

The laser excitation system as a light source may contain one, two, three, or more laser sources. The laser may be a solid state, diode pumped, frequency doubled Nd: YAG (Neodymium-doped Yttrium Aluminum Garnet) or YVO4 laser producing green laser light, having a wavelength of 532 nm or other laser implementation. The light source may be within the excitation range of one or more fluorescent moieties to be excited on the chemical array. The wavelength of the excitation light provided by the light source may be tunable such to enable the use multiple color assays (i.e. employing multiple fluorescent moieties with distinct ranges of excitation and emission wavelengths). Further examples of tunable sources are described in U.S. Pat. No. 7,148,492, which is hereby incorporated by reference herein in its entirety for all purposes. Those of ordinary skill in the related art will appreciate that other types of light source may be employed in the subject system such as incandescent sources, one or more light emitting diodes (e.g. LED's), halogen or xenon sources, metal halide sources, or other sources known in the art.

The array-holding stage, as mentioned above, is positioned in the system such that light from the light source passes through the lens of the lens stage and onto a chemical array mounted on the array-holding stage. In certain embodiments, there may be an optical assembly to direct and focus light beam from the light source onto the surface of an array mounted on the array-holding stage. In certain cases, the chemical array is mounted on a motion array-holding stage in the same plane as the bracket in the lens stage. With reference to the Cartesian coordinates shown in FIG. 1, the array-holding stage would be in the plane of the x and y axes, and normal to the z axis. A processor may be operably connected to the stage so that the stage translates in an x and/or y direction, or in any combination of these directions.

In certain embodiments, an autofocus detector is provided to sense and correct any offset between different regions of the chemical array mounted on the array-holding stage and the focal plane of the system during scanning. An autofocus system may include a detector, a processor, and a motorized adjuster to move the stage in a direction closer or further from the lens in the linearly moveable lens assembly (e.g. z-axis in FIG. 1). The distance of the stage from the optical assembly and/or the lens in the lens stage can be controlled by a distance-control mechanism that moves the stage in a direction perpendicular to the plane of the scanner (e.g. to the plane of the x and y axes in FIG. 1).

Coupled to the stage may be a dynamic autofocus system which functions as a continuous function of z-position. If the plane of the surface of a mounted chemical array is not parallel to the plane of the surface of the stage, then translations in the x and y axes of the stage may also affect the distance between light-emitting moieties on the surface of the chemical array and the lens/optical assembly. The dynamic autofocus feedback-control mechanism can dynamically adjust the z-position of the stage as the stage is translated in the plane of x and y axes in order to correct for the small focus-distance variation during a scan due to chemical-array-surface irregularities and positioning and orientation problems that cause the plane of the surface of the chemical array to be inclined with respect to the plane of the surface of the stage.

As mentioned above, the stage in the subject system may be moved in the x and y axes and focused in the z-position as shown in FIG. 1. An actuator system may be coupled to the stage that moves the stage the same plane as bracket but perpendicular to the movement of the moving coil. For example, as shown in FIG. 1, since the moving coil moves back and forth in the x-axis, the actuator system may move the stage in the y-axis. This movement of the array-holding stage in combination with the movement of the moving coil allows a 2-D raster-type scanning pattern of the mounted chemical array.

The depth of field in such scanning may vary and in certain cases, ranges from about 1000 microns to about one micron or less. A scanline (i.e. scanplane) in a 2-D raster scanning pattern refers to a single row of pixels that are generated from data collected from light emitted from a chemical array when the scanner system has scanned across a length of the array. After each scanline is scanned once or repetitively scanned multiple times, the array-holding stage moves in the Y-axis, as indicated by the Cartesian coordinate in FIG. 1, to the next scanline. The scanner can then excite the mounted chemical array and collect data in successive y positions. As the array-holding stage moves the array successively in all the y positions, an image may be constructed from data derived from multiple rows of pixels. Depending on the array size, number of arrays mounted on stage and the region of interest to be scanned, different number of scanlines and the length of a scanline may vary. In certain cases, arrays are often scanned and/or scan results are often represented between 1 and 10 micron pixel resolution, e.g., 5, 4, 3, 2, or up to 1 micron. Details of raster scanning may be found in the art, e.g. U.S. Pat. No. 5,144,477, disclosure of which is incorporated herein by reference in its entirety.

The scanner system may also contain a system for detecting the position of the lens mounted in bracket of the lens stage. Since the lens in the bracket moves back and forth during scanning operation, a position sensitive device, (e.g. a linear encoder) may be useful in keeping the back and forth movement in coordination with the operation relating to excitation and data collection, for example. PSD may also to detect positions of any components in the subject scanner system other than the moving lens, e.g. light beams, optical components, array-holding stage. PSDs may be of various types. For example, the PSD may be a linear encoder that contains sensor surface that has a raster-like structure that supplies continuous position data or a surface that supply local discrete data. More details on PSD may be found in U.S. Pat. No. 6,292,257 and U.S. Pat. No. 5,973,798, disclosures of which are incorporated herein by reference.

As noted above, the scanner system comprises the subject lens stage described previously. The lens stage may be incorporated in the scanner system in a configuration to allow excitation light from the light source to passes through the lens of the device and onto a chemical array mounted on the array-holding stage.

The scanner system also comprises one or more photodetectors. The photodetector may be of different types, including photo-multiplier tubes, charge-coupled devices, and avalanche photodiodes. There may be a photodetector for each laser scanning station. The photodetector is mounted so that it does not block or otherwise interfere with the outgoing or incoming light rays reflecting off any of components of an optical assembly or the chemical array mounted in the system during laser scanning and light collecting operations. The analog scan signal produced from each photodetector is processed in a conventional manner in an analog data processing board.

The pixel signal intensity data collected from a chemical array may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

In certain embodiments, the scanner system is configured such that the direction in which the moving coil moves linearly back and forth is orthogonal to a horizontal surface on which the scanner system resides. For example, if the scanner system is placed on a table top with the horizontal surface parallel to the surface of the earth, the direction in which the moving coil moves would be perpendicular to the table top (i.e. "up and down" relative to the table top). In certain embodiments, this configuration minimizes vibration caused by the movement of the lens stage during operation of the scanner system.

While it is noted that a scanner that reverses scanning direction at the end of each scan line (i.e. a bi-directional scanner) is disclosed, unidirectional scanners also find use with the methods of the invention.

Representative scanners of interest include those described in U.S. Pat. Nos. 5,585,639; 5,760,951; 5,763,870; 6,084,991; 6,222,664; 6,284,465; 6,329,196; 6,371,370 and 6,406,849, US Patent Pub No. 20060031029, the disclosures of which are herein incorporated by reference.

Figure 3:
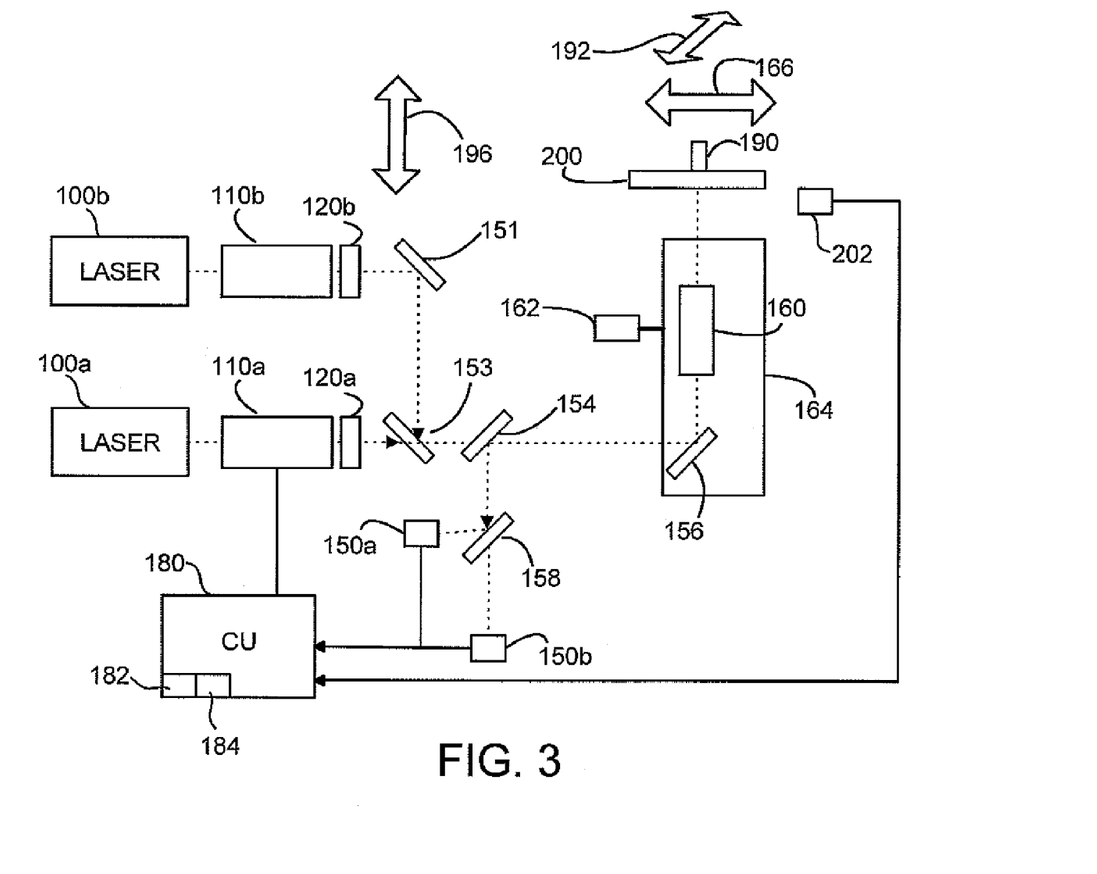
FIG. 3 schematically illustrates an exemplary scanner system that employs a subject lens stage.

An exemplary scanner as may be used in the present invention is shown in FIG. 3. Referring now to FIG. 3, an exemplary apparatus of the present invention (which may be generally referenced as an "array scanner") is illustrated. A light system provides light from a laser 100 which passes through an electro-optic modulator (EOM) 110 with attached polarizer 120. Each laser 100$a$, 100$b$ may be of different wavelength (e.g., one providing red light and the other green) and each has its own corresponding EOM 110$a$, 110$b$ and polarizer 120$a$, 120$b$. The beams may be combined along a path toward a holder or caddy 200 by the use of full mirror 151 and dichroic mirror 153. A control signal in the form of a variable voltage applied to each corresponding EOM 110$a$, 110$b$ by the controller (CU) 180, changes the polarization of the exiting light which is thus more or less attenuated by the corresponding polarizer 120$a$, 120$b$. Controller 180 may be or include a suitably programmed processor. Thus, each EOM 110 and corresponding polarizer 120 together act as a variable optical attenuator which can alter the power of an interrogating light spot exiting from the attenuator. The remainder of the light from both lasers 100$a$, 100$b$ is transmitted through a dichroic beam splitter 154, reflected off fully reflecting mirror 156 and focused onto an array mounted on holder 200, using optical components in beam focuser 160. Light emitted (in particular, fluorescence) at two different wavelengths (e.g., green and red light) from features on the array, in response to the interrogating light, is imaged using the same optics in focuser/scanner 160, and is reflected off mirrors 156 and 154. The two different wavelengths are separated by a further dichroic mirror 158 and are passed to respective detectors 150$a$ and 150$b$. Depending on how the subject methods are implemented, a subject scanner may contain more than one of 150$a$, and more than one of 150$b$, or, in alternate embodiments, 150$a$ and 150$b$ may be multi-gain detectors.

More optical components (not shown) may be used between the dichroic and each detector 150$a$, 150$b$ (such as lenses, pinholes, filters, fibers, etc.) and each detector 150$a$, 150$b$ may be of various different types (e.g., a photo-multiplier tube (PMT), or photodiode or avalanche photodiode device (APD), such as a charge-coupled device (CCD), a charge-injection device (CID), or a complementary-metal-oxide-semiconductor detector (CMOS) device), CCD or an avalanche photodiode (APD). All of the optical components through which light emitted from an array or calibration member in response to the illuminating laser light, passes to detectors 150$a$, 150$b$, together with those detectors, form a detection system. This detection system has a fixed focal plane. A scan system causes the illuminating region in the form of a light spot from each laser 100$a$, 100$b$, and a detecting region of each detector 150$a$, 150$b$ (which detecting region will form a pixel in the detected image), to be scanned across multiple regions of an array or array package mounted on holder 200. The scanned regions for an array will include at least the multiple features of the array. In particular the scanning system is typically a line by line scanner, scanning the interrogating light in a line across an array when at the reading position, in a direction of arrow 166, then moving ("transitioning") the interrogating light in a direction into/out of the paper as viewed in FIG. 3 to a position at an end of a next line, and repeating the line scanning and transitioning until the entire array has been scanned. This movement may employ the subject lens stage described previously.

This scanning feature is accomplished by providing a housing 164 containing mirror 158 and focuser 160, which housing 164 can be moved along a line of pixels (i.e., from left to right or the reverse as viewed in FIG. 3) by a transporter 162. The second direction 192 of scanning (line transitioning) can be provided by second transporter which may include a motor and belt (not shown) to move caddy 200 along one or more tracks. The second transporter may use a same or different actuator components to accomplish coarse (a larger number of lines) movement and finer movement (a smaller number of lines). Generally, directly adjacent rows are scanned. However, "adjacent" rows may include alternating rows or rows where more than one intervening row is skipped.

The scanner of FIG. 3 may further include a reader (not shown) which reads an identifier from an array package. When identifier is in the form of a bar code, that reader may be a suitable bar code reader.

The system may also include detector 202, processor 180, and a motorized or servo-controlled adjuster 190 to move holder 200 in the direction of arrow 196 to establish correct focus for the system. The detector may directly detect a partial reflection from another beamsplitter (not shown) between splitters 153 and 154. In addition, autofocus system 202 may contain a position detector e.g. a quadrature position encoder, also feeding back to the CU measures the absolute position (i.e., relative to the apparatus) of the servo-controlled adjuster 190. As above with respect to movements 166 and 192, it should be observed that focus servo control movement 196 may occur in connection with housing 164 instead of the holder, or, if the detection system is not a fixed focal plane system, by an adjustment of laser focuser 160. Further details regarding suitable chemical array autofocus hardware is described in pending U.S. patent application Ser. No. 09/415,184 for "Apparatus And Method For Autofocus" by Dorsel, et al., filed Oct. 7, 1999, as well as European publication EP 1091229 published Apr. 11, 2001 to the same title and inventors.

Controller 180 of the apparatus is connected to receive signals from detectors 150a, 150b (these different signals being different "channels"), namely a signal which results at each of the multiple detected wavelengths from emitted light for each scanned region of array when at the reading position mounted in holder 200. Controller 180 also receives the signal from autofocus detector 202, and provides the control signal to EOM 110, and controls the scan system. Controller 180 contains all the necessary software to detect signals from detector 202, and regulate a motorized or servo-controlled adjuster 190 through a control loop. Controller 180 may also analyze, store, and/or output data relating to emitted signals received from detectors 150a, 150b in a known manner.

Controller 180 also includes a programmable digital signal processor for performing the methods described above, e.g., a current-to-voltage converter, voltage amplifier, etc., as desired, a media reader 182 which can read a portable removable media (such as a magnetic or optical disk), and a communication module 184 which can communicate over a communication channel (such as a network, for example the internet or a telephone network) with a remote site (such as a database at which information relating to array package may be stored in association with the identification).

In one mode of operation, an array in a package is typically first exposed to a liquid sample. This liquid sample may be placed directly on the array or introduced into a chamber through a septa in the housing of the array. After a time to allow, for example, hybridization, the array may then be washed and scanned with a liquid (such as a buffer solution) present in the chamber and in contact with the array, or it may be dried following washing. After mounting a given array in cradle 200 (either with the array features on the glass surface nearer to, or further from, the lens—depending, at least, upon the lens setup) the identifier reader may automatically (or upon operator command) read an identifier from the array package, which may be used to e.g. retrieve information on the array layout from a database containing the identifier in association with such information. Such a database may be a local database accessible by controller 180 (such as may be contained in a portable storage medium in drive 182.

Methodology

A method for scanning a chemical array is also provided. In one embodiment, the method involves: a) placing a chemical array in the scanner system described previously; and b) scanning the array.

In certain cases, scanning the array involves moving the lens stage back and forth to focus light successively onto different region on the surface of a chemical array mounted on an array holding stage. In some embodiments, an optical assembly in conjunction with the lens helps focus excitation light onto a specific region of the chemical array and also helps reflect emitted light to a photodetector. Each of a plurality of regions of an array may be excited and data from each region may be collected one at a time in order to improve resolution of the array image. The back and forth movement of the lens stage allows excitation and collection of data in one specific region at a time in a successive manner such that a collection of data over a plurality of regions may be collected over multiple scanlines. Using the subject lens stage in the method provided herein thus may allow a precise excitation and measurement for all of the regions on the chemical array in a short amount of time.

One embodiment of the scanning method is described in detail below. Each time a lens stage moves across a length of the array (e.g. in the x-direction of FIG. 1), one scanline is made and data from a row of pixels are collected. Sometimes, the same scanline may be scanned repetitively. After one scanline, the array-holding stage moves orthogonal to the direction of the movement of the moving coil (e.g. in the y-direction) so the next scanline in a different y-position on the array is scanned. In certain embodiments, each scanline may not traverse across a full length of an area that needs to be scanned but are broken up into swaths. For example, an I×j pixel image of a chemical array may be constructed by scanning over the array in contiguous parallel swaths, in which I may represent a dimension in the y-axis and j represents a dimension in the x-axis. Accordingly, there are j÷I scan lines for each swath. Each swath detects I×n pixels where n is the width of a swathe and is a number smaller than the whole length represented by j. When j÷n swaths are scanned, an I×j pixel image may be constructed. In some cases, j÷n' swaths are scanned, where n' is somewhat smaller than n to allow for overlaps between adjacent swaths. The scanning method presented above may be modified to accommodate different types of system and chemical array experiments. Other information relating to scanning may be found in the art, e.g. U.S. Pat. No. 6,417,936.

Utility

The subject lens stage and system and methods associated within find use in a variety of applications, where such applications are generally a scanning system for chemical array analysis. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present disclosure. The presence of the analyte in the sample is then deduced from the detection of binding complexes on the substrate surface.

As noted above, the moving coil in the lens stage may expand in size due to thermal expansion during a scanning operation. In employing the subject lens stage that contains a means for reducing the force exerted by thermal expansion onto other device components of the lens stage (e.g. bearing cars), the efficiency and integrity of the scanning system may be increased. Accordingly, the subject lens stage and system and methods associated within finds use in many scanning methods affected by thermal expansion.

Specific chemical array scanning applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a programmed scanner according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. Certain embodiments of the invention may involve transmitting data obtained from a method described above from a first location to a remote location. Certain other embodiments of the invention may involve receiving, from a remote location, data obtained from a method described above.

All publications and patents cited in this specification herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A lens stage comprising:
 a) a support comprising a first rail and a second rail, wherein said first rail and said second rail are mounted to said support in parallel; and
 b) a linearly moveable lens assembly comprising:
  i) a voice coil comprising a moving coil that moves in a direction parallel to said rails;
  ii) a lens;
  iii) a bracket that is attached to: a) said moving coil and b) said lens, and moveably engaged with said rails via a set of bearing cars; and
  iv) means to reduce force exerted on said set of bearing cars due to thermal expansion of said moving coil, wherein said means to reduce force is selected from:
   a flexure in said bracket proximal to said moving coil, wherein said flexure allows said bracket to bend in response to said thermal expansion; and
   a precision shoulder screw that connects said bracket to said moving coil, wherein thermal expansion of said moving coil moves said shoulder screw through an orifice of said bracket without moving said bracket.

2. The lens stage of claim 1, wherein said precision shoulder screw comprises a first region and a second region, wherein said first region is embedded in said moving coil and said second region is present in said orifice of said bracket.

3. The lens stage of claim 2, wherein said first region of said precision shoulder screw is embedded via threading.

4. The lens stage of claim 1, wherein said linearly moveable lens assembly travels back and forth in a direction that is parallel to said rails, wherein said lens is at the center of gravity of said linearly moveable lens assembly.

5. The lens stage of claim 1, wherein said bracket is aluminum, magnesium or an alloy thereof.

6. The lens stage of claim 1, wherein said lens stage further comprises a positional detector that senses the position of said moving coil on said rails.

7. A chemical array scanner comprising:
 a) a light source;
 b) a stage for holding a chemical array;
 c) a lens stage comprising a support comprising a first rail and a second rail, wherein said first rail and said second rail are mounted to said support in parallel, and a linearly moveable lens assembly comprising:
  i) a voice coil comprising a moving coil that moves in a direction parallel to said rails;
  ii a lens;
  iii) a bracket that is attached to said moving coil and said lens, and moveably engaged with said rails via a set of bearing cars; and iv) means to reduce force exerted on said set of bearing cars due to thermal expansion of said moving coil; and d) a photodetector, wherein said scanner is configured so that light from said light source passes through said lens to a chemical array positioned in said stage, and that light emitted by said chemical array passes through said lens and is detected by said photodetector.

8. The scanner of claim 7, wherein said moving coil moves in a direction perpendicular to the surface upon which the chemical scanner is positioned.

9. The scanner of claim 7, wherein said stage is coupled to an actuator system that moves said stage in a direction perpendicular to said moving coil in the plane of said array, thereby allowing said chemical array be scanned by rastering.

10. The scanner of claim 7, where said scanner further comprises an optical assembly to direct light from said light source to said chemical array.

11. The scanner of claim 7, wherein said scanner further comprises an autofocus system that maintains focus of said lens on an illuminated region of said chemical array.

12. The scanner of claim 7, wherein said scanner further comprises a computer for executing instructions for scanning said chemical array.

13. The scanner of claim 7, wherein said scanner further comprises a computer for storing data obtained from scanning said chemical array.

14. A method of scanning comprising:

a) placing a chemical array in the scanner of claim 7; and b) scanning said chemical array.

15. The method of claim 14, wherein said scanning comprises raster scanning.

16. The method of claim 14, wherein said method further comprise collecting signals emitted by said chemical array.

17. The method of claim 14, wherein said moving coil thermally expands during said scanning.

* * * * *

UNITED STATES PATENT AND TRADEMARK OFFICE
CERTIFICATE OF CORRECTION

PATENT NO. : 8,213,069 B2
APPLICATION NO. : 12/494041
DATED : July 3, 2012
INVENTOR(S) : Lawrence J. DaQuino et al.

It is certified that error appears in the above-identified patent and that said Letters Patent is hereby corrected as shown below:

In column 18, line 64, in Claim 7, delete "ii" and insert -- ii) --, therefor.

In column 19, line 17, in Claim 10, delete "where" and insert -- wherein --, therefor.

Signed and Sealed this
Fourteenth Day of August, 2012

David J. Kappos
*Director of the United States Patent and Trademark Office*